(12) United States Patent
Yang et al.

(10) Patent No.: US 11,420,932 B2
(45) Date of Patent: Aug. 23, 2022

(54) METHOD FOR PREPARING PREGABALIN INTERMEDIATE (R)-3-(CARBAMOYLMETHYL)-5-METHYL-HEXANOIC ACID

(71) Applicant: ZHEJIANG HUAHAI PHARMACEUTICAL CO., LTD, Zhejiang (CN)

(72) Inventors: Changming Yang, Zhejiang (CN); Pan Guo, Zheijang (CN); Yifeng Wang, Zheijang (CN); Wenling Zhang, Zheijang (CN); Peng Wang, Zheijang (CN)

(73) Assignee: ZHEIJIANG HUAHAI PHARMACEUTICAL CO., LTD., Zhejiang (CN)

( * ) Notice: Subject to any disclaimer, the term of this patent is extended or adjusted under 35 U.S.C. 154(b) by 0 days.

(21) Appl. No.: 17/112,891

(22) Filed: Dec. 4, 2020

(65) Prior Publication Data
US 2021/0114970 A1 Apr. 22, 2021

Related U.S. Application Data

(63) Continuation of application No. PCT/CN2018/090068, filed on Jun. 6, 2018.

(51) Int. Cl.
*C07C 227/06* (2006.01)
*C12P 13/02* (2006.01)

(52) U.S. Cl.
CPC ............ *C07C 227/06* (2013.01); *C12P 13/02* (2013.01)

(58) Field of Classification Search
CPC ..... C07C 227/06; C07C 227/04; C12P 13/02; C12P 7/40
See application file for complete search history.

(56) References Cited

U.S. PATENT DOCUMENTS

2010/0087525 A1* 4/2010 Hedvati ................... C12P 7/62
435/135

FOREIGN PATENT DOCUMENTS

| CN | 101268037 | 9/2008 |
| CN | 102465157 | 5/2012 |

(Continued)

OTHER PUBLICATIONS

Extended European Search Report on EP Appl. Ser. No. EP 18921480.2 dated Dec. 20, 2021 (25 pages).

(Continued)

*Primary Examiner* — Deborah D Carr
(74) *Attorney, Agent, or Firm* — Foley & Lardner LLP

(57) ABSTRACT

A method for preparing pregabalin chiral intermediate (R)-3-(carbamoylmethyl)-5-methylhexanoic acid by a biological enzyme method. In particular, the method comprises: reacting compound (I) 3-isobutylglutaric acid, as a raw material, with a nitrogen-containing agent to produce compound (II) 3-isobutylglutarimide; and performing stereoselective ring-opening of compound (II) under the action of a biological enzyme to produce compound (III) (R)-3-(carbamoylmethyl)-5-methylhexanoic acid:

(Continued)

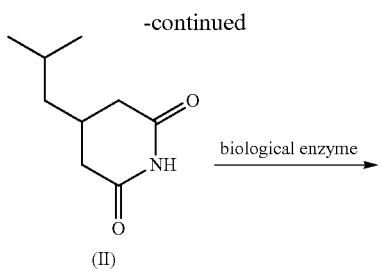

-continued (II)

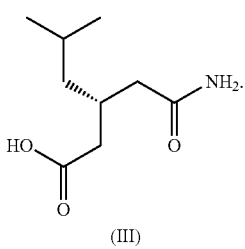

(III)

13 Claims, 1 Drawing Sheet

(56) References Cited

FOREIGN PATENT DOCUMENTS

| CN | 105348123 | 2/2016 |
|---|---|---|
| WO | WO-2015/141758 A1 | 9/2015 |
| WO | WO2019/232706 | 12/2019 |

OTHER PUBLICATIONS

Nojiri Masutoshi et. al., "Imidase catalyzing desymmetric imide hydrolysis forming optically active 3-substituted glutaric acid monoamides for the synthesis of gamma-aminobutryric acid (GABA) analogs", Applied Microbiology and Biotechnology, Springer Berlin Heidelberg, Berlin/Heidelberg, vol. 99, No. 23, Jul. 24, 2015, pp. 9961-9969.

Yamamoto Yukio et. al., "Asymmetric Synthesis of Optically Active Lactones from Cyclic Acid Anhydrides Using Lipase in Organic Solvents", Agric. Biol. Chem., vol. 52, No. 12, Jul. 4, 1988, pp. 3087-3092.

International Search Report regarding Application No. PCT/CN2018/090068 dated Feb. 27, 2019; 4 pages.

* cited by examiner

METHOD FOR PREPARING PREGABALIN INTERMEDIATE (R)-3-(CARBAMOYLMETHYL)-5-METHYL-HEXANOIC ACID

CROSS-REFERENCE TO RELATED APPLICATIONS

This application is a Continuation of PCT/CN2018/090068, filed on Jun. 6, 2018, the entire disclosure of which is incorporated herein by reference.

TECHNICAL FIELD

The present invention relates to a technology for preparing pregabalin chiral intermediates, specifically relates to a method for preparing pregabalin chiral intermediate (R)-3-(carbamoylmethyl)-5-methylhexanoic acid under biological enzymatic catalysis.

BACKGROUND

The chemical name of pregabalin is (S)-(+)-3-aminomethyl-5-methylhexanoic acid, which is the pharmacologically active S-isomer of 3-aminomethyl-5-methylhexanoic acid. The structure of pregabalin is as follows:

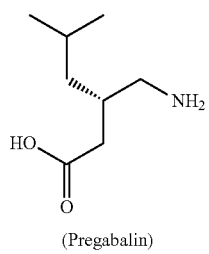

(Pregabalin)

Pregabalin is a 3-isobutyl substituted neurotransmitter GABA (γ-aminobutyric acid) developed by Pfizer from the United States. Pregabalin is a new type of calcium channel modulator with good fat solubility and can pass through the blood-brain barrier. Pregabalin is mainly used for the treatment of peripheral neuralgia and for adjuvant treatment of focal seizure. The drug has good analgesic effects, small toxic and side effects, and does not cause drug interaction with existing antiepileptic drugs. The drug can produce a synergistic effect through drug combination, is applicable to a wide range of people, and has broad market development prospects.

The S-isomer of pregabalin has the pharmacological activity, and the activity of the R-isomer thereof is only 1/10 of that of the S-isomer. In the chemical synthesis process of pregabalin, 3-(carbamoylmethyl)-5-methylhexanoic acid is a very important intermediate. After chiral resolution of this intermediate, (R)-3-(carbamoylmethyl)-5-methylhexanoic acid is obtained, and then Hofmann degradation is carried out to remove the carbonyl to obtain (S)-(+)-3-aminomethyl-5-methylhexanoic acid, namely pregabalin.

The preparation of 3-(carbamoylmethyl)-5-methylhexanoic acid currently reported in the literatures adopts the following synthetic methods:

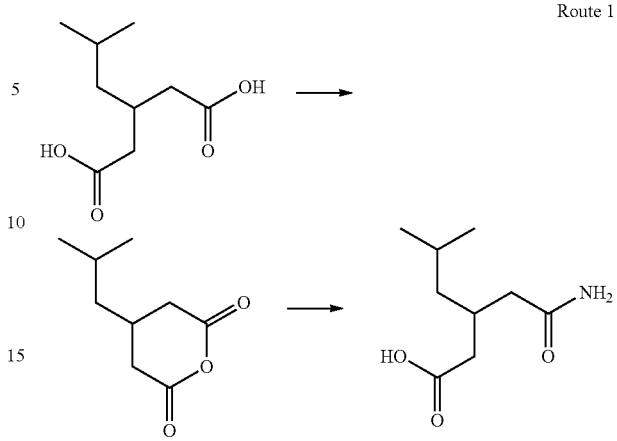

Route 1

3-isobutylglutaric acid is dehydrated and cyclized under the action of dehydrating agent acetic anhydride or acetyl chloride to obtain 3-isobutylglutaric anhydride; 3-isobutylglutaric anhydride undergoes ammonolysis reaction to obtain 3-(carbamoylmethyl)-5-methylhexanoic acid;

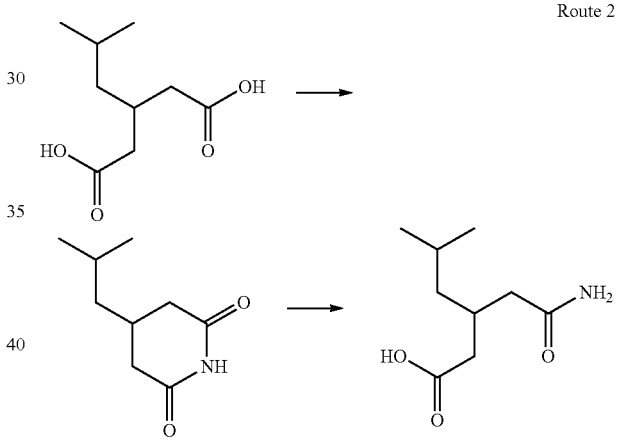

Route 2

3-isobutylglutaric acid reacts with a nitrogen-containing reagent at high temperature to close the ring to obtain 3-isobutylglutarimide; 3-isobutylglutarimide is hydrolyzed and ring-opened under basic condition to obtain 3-(carbamoylmethyl)-5-methylhexanoic acid.

The 3-(carbamoylmethyl)-5-methylhexanoic acid prepared according to the above-mentioned process routes is racemate, which needs to be resolved to obtain the chiral intermediate (R)-3-(carbamoylmethyl)-5-methylhexanoic acid required for the preparation of pregabalin, then Hofmann degradation is carried out to obtain pregabalin:

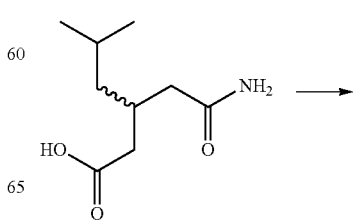

-continued

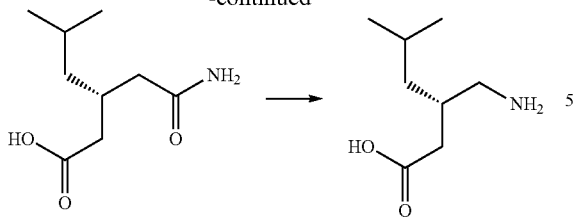

SUMMARY

The second route is referred by the present invention, firstly preparing 3-isobutylglutarimide from 3-isobutylglutaric acid as the starting material, and performing stereoselective ring-opening of 3-isobutylglutarimide under the catalysis of a biological enzyme to directly obtain the chiral intermediate (R)-3-(carbamoylmethyl)-5-methylhexanoic acid required for the preparation of pregabalin.

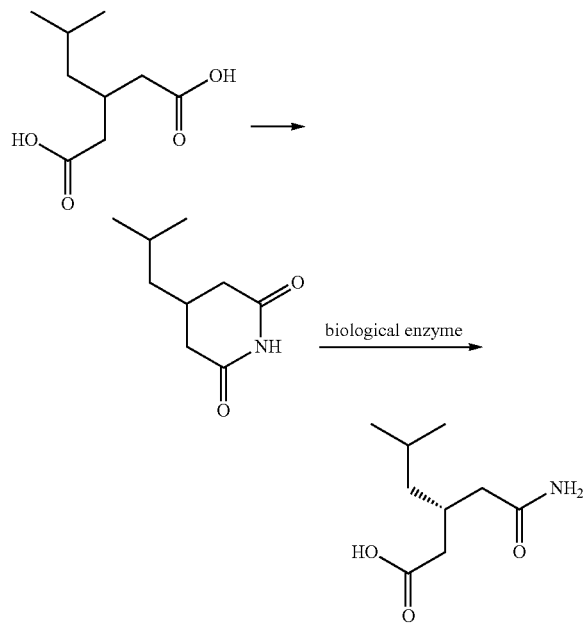

Compared with the existing methods reported in the literatures, the method provided by the present invention eliminates the resolution step from 3-(carbamoylmethyl)-5-methylhexanoic acid to (R)-3-(carbamoylmethyl)-5-methylhexanoic acid, shortens the process route, reduces the production cost, has the advantages of mildness, high efficiency, and environmental protection. The obtained chiral intermediate has high optical purity, which can provide high-quality and low-cost raw materials for the further synthesis of pregabalin, and has high industrial and economic value.

The purpose of the present invention is to provide a new synthetic method for preparing pregabalin chiral intermediate (R)-3-(carbamoylmethyl)-5-methylhexanoic acid.

In order to achieve the above objective, the present invention adopts the following technical solutions:

A method for preparing pregabalin intermediate (R)-3-(carbamoylmethyl)-5-methylhexanoic acid, which comprises the following steps:

step 1):

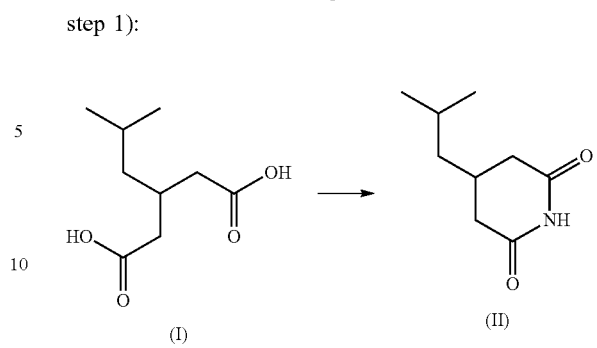

For step 1), the synthesis methods in patent documents CN 1884263A and CN 106045873A can be referred to, which are specifically as follows:

Reacting compound (I) 3-isobutylglutaric acid with a nitrogen-containing reagent (ammonia water, urea, a basic ammonium salt or thiourea) to produce compound (II) 3-isobutylglutarimide; the reaction of step 1) can be carried out in an organic solvent selected from toluene, xylene and octane, etc., and the ratio of the volumetric amount of the organic solvent to the mass amount of 3-isobutylglutaric acid is 2:1-6:1; the ratio of the mass amount of nitrogen-containing reagent to the mass amount of 3-isobutylglutaric acid is 0.2:1-0.6:1. The specific reaction comprises stirring and heating to 100-140° C., keeping the temperature, refluxing and stirring for 2-5 h, cooling to 0-15° C., stirring and crystallizing for 1 h, filtering and drying to obtain compound (II); or heating to 100-200° C., reacting for not less than 2 h, cooling to 80-90° C., adding purified water, ethanol and activated carbon, heating to reflux for 30 min-0.5 h, filtering, cooling the filtrate to crystallize, filtering and drying to obtain compound (II).

Step 2):

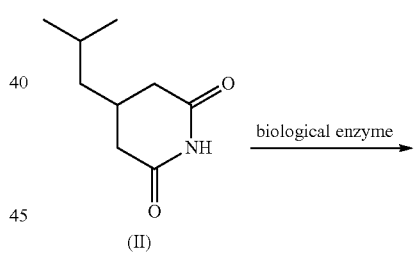

Adding the compound (II) obtained in step 1) into a solvent, performing stereospecific ring-opening through the selectively oriented breakage of the amide bond in the molecular structure and under the action of a biological enzyme to produce compound (III) (R)-3-(carbamoylmethyl)-5-methylhexanoic acid.

In step 2), the biological enzyme is a hydrolase, specifically a specific type of lipase or esterase.

The lipase can be plant lipases such as lipase from *Carica papaya*; or animal lipases such as lipase from porcine pancreatic; or bacterial lipases such as lipase from *Burk-* holderia cepacia, lipase from *Pseudomonas cepacia*; or fungal lipases such as lipase from *Candida rugosa*, lipase from *Rhizomucor miehei*, lipase from *Aspergillus oryzae*. Among the above-mentioned lipases, lipase from *Carica papaya*, lipase from *Pseudomonas cepacia* and lipase from *Candida rugosa* are preferred.

The esterase can be thermophilic esterase APE1547, ethyl chrysanthemate esterase, esterase EST12-7 from the deep sea of South China Sea, liver esterase or carboxylesterase. Among the above-mentioned esterases, ethyl chrysanthemate esterase and esterase EST12-7 from the deep sea of South China Sea are preferred.

In step 2), the form of the biological enzyme can be immobilized enzyme particles or enzyme powder after freeze-drying, or enzyme-containing cells or organelles after extraction, concentration and dehydration processes. The enzymes used can be commercial enzymes or crude enzymes obtained by culturing enzyme-producing microorganisms.

In step 2), the mass ratio of the biological enzyme and compound (II) is 1:1-1:20; preferably 1:5-1:10.

In step 2), the solvent is a miscible system of purified water and organic solvent. The organic solvent can be alcohols, ethers or ketones; preferably one or more of alcohols such as ethanol, isopropanol, cyclohexanol, ethers such as tetrahydrofuran, 1,4-dioxane, and ketones such as acetone, cyclohexanone ("more" in the present application refers to two or more than two), and more preferably ethanol, tetrahydrofuran and acetone; preferably, as to the mixing ratio of purified water to organic solvent in the miscible system of water and organic solvent, the mass ratio of purified water to organic solvent is 1:1-1:5, and more preferably 1:2. The mass ratio of compound (II) to the solvent is 1:5-1:50, preferably 1:5-1:10.

In step 2), the reaction temperature is 25-55° C., preferably 30-45° C.

In step 2), the reaction time is 8-20 h, preferably 10-15 h.

In step 2), after the reaction, the biological enzyme used can be separated by simple filtration and reused.

In step 2), the optical purity of the reaction product is detected by chiral high performance liquid chromatography. The chromatographic conditions are as follows: chromatograph: Aglient HPLC 1260; detector: UV variable wavelength detector, detection wavelength 210 nm; chromatographic column: Supelco Discovery RP amide (150×4.6 mm, 5 μm), column temperature 30° C.; mobile phase, buffer solution: acetonitrile=80:20 (% V/V), wherein the buffer solution is 0.02 M aqueous solution of ammonium dihydrogen phosphate, adjusted to pH 3.0 with phosphoric acid; flow rate: 1.5 mL/min; injection volume: 20 μL.

The present invention also provides a method for preparing pregabalin, which comprises the above steps 1) and 2), and also comprises a step of obtaining pregabalin through the Hoffman degradation reaction of the obtained (R)-3-(carbamoylmethyl)-5-methylhexanoic acid under the action of bromine and a base.

The present invention provides a new method for preparing pregabalin chiral intermediates: 3-isobutylglutarimide obtained by cyclization of 3-isobutylglutaric acid is stereoselectively ring-opened under the action of a biological enzyme to directly obtain (R)-3-(carbamoylmethyl)-5-methylhexanoic acid, eliminating the resolution operation of 3-(carbamoylmethyl)-5-methylhexanoic acid, which reduces the production cost, improves the production efficiency and has the advantages of environmental protection. The obtained product has high optical purity and is easy for industrial production.

DETAILED DESCRIPTION

In order to better understand the content of the present invention, the technical solutions of the present invention will be described below with specific examples, but the scope of protection is not limited thereto.

In the described examples, the compound (I) 3-isobutylglutaric acid used in step 1) is a commercial available chemical; the biological enzyme used in step 2) is a commercial enzyme or a freeze-dried enzyme powder provided by a relevant research institution.

The specific embodiments of the present invention will be detailed described below in conjunction with the examples. The following examples are only used to illustrate the present invention, but not to limit the scope of the present invention.

Step 1) in the following examples refers to the synthesis methods in patent documents CN 1884263A and CN 106045873A.

EXAMPLE 1

Figure 1:
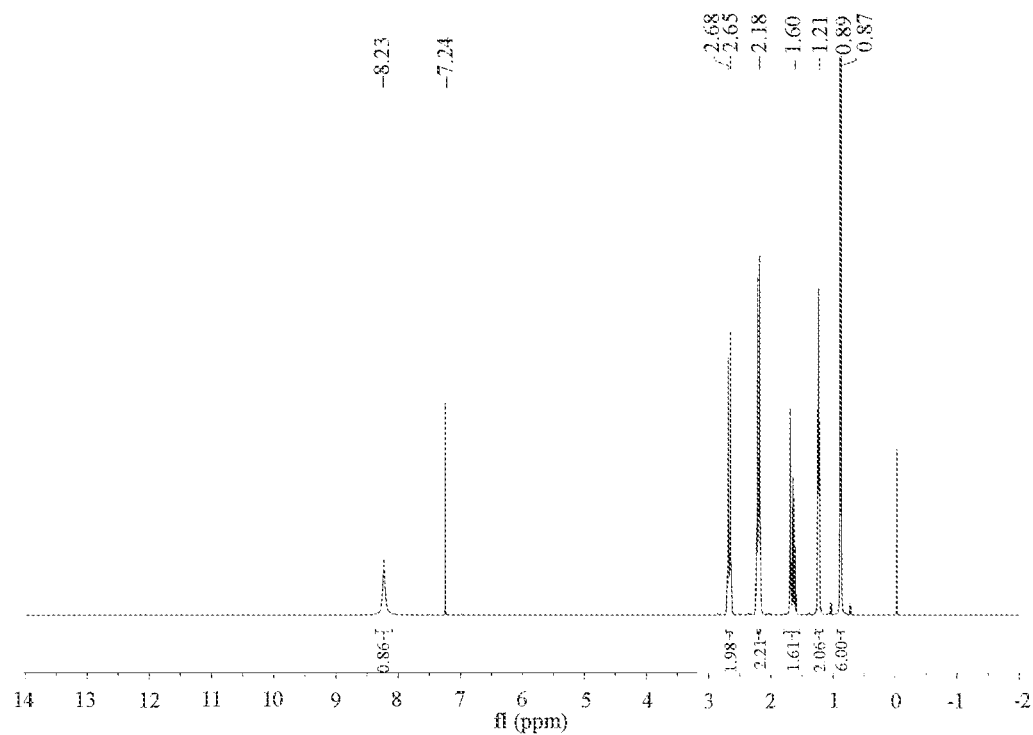
FIG. 1 is the NMR spectrum of compound (II) prepared in Example 1.

Step 1): Preparation of 3-isobutylglutarimide: 50 g of compound (I) 3-isobutylglutaric acid (producer: Dayang Chem (Hangzhou) Co., Ltd., purity 98%), 200 mL of toluene and 20 g of urea were added into a reaction flask, stirred and heated to 110° C., the temperature was kept, refluxed and stirred for 3 h, cooled to 5-15° C., stirred and crystallized for 1 h, filtered and dried to obtain 41.6 g of compound (II) 3-isobutylglutarimide with a yield of 92.1%. The NMR spectrum of compound (II) is shown in FIG. 1, and the chemical structure is confirmed to be compound (II) 3-isobutylglutarimide.

Figure 2:
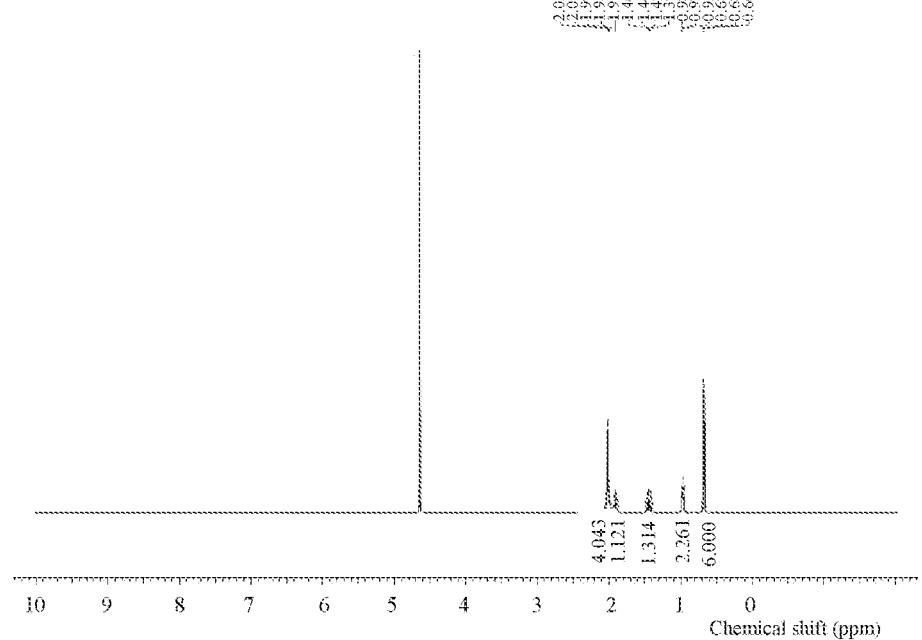
FIG. 2 is the NMR spectrum of compound (III) prepared in Example 1. Wherein, collection time (seconds): 3.4079; frequency (MHz): 399.7674; core: 1H; transient count: 64; original point count: 16384; point count: 16384; pulse sequence: s2pul; receiver gain: 18.00; SW (periodic) (Hz): 4807.69; solvent: deuterium oxide; spectral line shift (Hz): 1599.0200; spectrum type: standard; sweep width (Hz): 4807.69; temperature (degrees Celsius): room temperature.

Step 2): Preparation of (R)-3-(carbamoylmethyl)-5-methylhexanoic acid: 40 g of compound (II) 3-isobutylglutarimide obtained in step 1) was added into a reaction flask, then 100 g of ethanol, 100 g of purified water, 4 g of lipase from *Carica papaya* (producer: Xuzhou Runhe Biotechnology Co., Ltd., purity 98%) were also added, heated to 30° C., the temperature was kept and stirred for 10 h. After the reaction, the lipase from *Carica papaya* was removed by filtration, the filtrate was concentrated under reduced pressure to ⅓ of the volume, the temperature was reduced to 0-5° C., filtered and dried to obtain 42.4 g of target product compound (III) (R)-3-(carbamoylmethyl)-5-methylhexanoic acid with a yield of 95.8%, product enantiomeric excess ee.=99.89%. The NMR spectrum of compound (III) is shown in FIG. 2, and the chemical structure is confirmed to be compound (III) (R)-3-(carbamoylmethyl)-5-methylhexanoic acid.

EXAMPLE 2

Step 1): Preparation of 3-isobutylglutarimide: 50 g of compound (I) 3-isobutylglutaric acid (producer: Dayang Chem (Hangzhou) Co., Ltd., purity 98%) and 55 g of 25% ammonia water were added into a reaction flask, the ammonia water was concentrated to dryness, heated to 100° C., reacted for 2 h, cooled to 80° C., 100 mL of purified water, 50 mL of ethanol and 3 g of activated carbon were added, heated to reflux for 0.5 h, filtered, the filtrate was cooled and crystallized, filtered and dried to obtain 40.0 g of compound (II) 3-isobutylglutarimide with a yield of 88.5%. The NMR spectrum of the product is the same as in FIG. 1.

Step 2): Preparation of (R)-3-(carbamoylmethyl)-5-methylhexanoic acid: 35 g of compound (II) 3-isobutylglutarimide prepared in step 1) was added into a reaction flask, then 232 g of tetrahydrofuran, 116 g of purified water and 7 g of lipase from *Pseudomonas cepacia* (producer: Shanghai KDN Biotech Co., Ltd., purity 98%) were also added, heated to 45° C., the temperature was kept and stirred for 15 h. After the reaction, the lipase from *Pseudomonas cepacia* was removed by filtration, the reaction solution was distilled under reduced pressure, concentrated until about ⅓ of the volume was left, cooled to 0-10° C., stirred and crystallized for 1 h, filtered and dried to obtain 37.2 g of target product compound (III) (R)-3-(carbamoylmethyl)-5-methylhexanoic acid with a yield of 96.1%, product enantiomeric excess ee.=99.93%. The NMR spectrum of the product is the same as in FIG. 2.

EXAMPLE 3

Step 1): Preparation of 3-isobutylglutarimide: 50 g of compound (I) 3-isobutylglutaric acid (producer: Dayang Chem (Hangzhou) Co., Ltd., purity 98%), 50 g of acetic anhydride and 40 g of ammonium acetate were added into a reaction flask, heated to 140° C. and refluxed for 4 h, the excess acetic anhydride and the resulting acetic acid were concentrated, cooled to 90° C., 15 mL of purified water, 15 mL of ethanol and 5 g of activated carbon were added, heated to reflux for 30 min, filtered, the filtrate was cooled and crystallized, filtered and dried to obtain 40.5 g of compound (II) 3-isobutylglutarimide with a yield of 89.6%. The NMR spectrum of the product is the same as in FIG. 1.

Step 2): Preparation of (R)-3-(carbamoylmethyl)-5-methylhexanoic acid: 30 g of compound (II) 3-isobutylglutarimide prepared in step 1) was added into a four-necked flask, then 135 g of acetone, 45 g of purified water and 5 g of lipase from *Candida rugosa* (producer: Hangzhou Novocata Biotechnology co., Ltd., purity 98%) were also added, heated to 40° C., the temperature was kept and stirred for 8 h. After the reaction, the lipase from *Candida rugosa* was removed by filtration, the reaction solution was distilled under reduced pressure, concentrated until about ⅓ of the volume was left, cooled to 0-10° C., stirred and crystallized for 1 h, filtered and dried to obtain 31.1 g of target product compound (III) (R)-3-(carbamoylmethyl)-5-methylhexanoic acid with a yield of 93.7%, product enantiomeric excess ee.=99.91%. The NMR spectrum of the product is the same as in FIG. 2.

EXAMPLE 4

Step 1): Preparation of 3-isobutylglutarimide: 50 g of compound (I) 3-isobutylglutaric acid (producer: Dayang Chem (Hangzhou) Co., Ltd., purity 98%) and 15 g of urea were added into a reaction flask, heated to 160° C. by oil bath, reacted under 160-180° C. for 2 h, cooled to 90° C., 15 mL of purified water, 15 mL of ethanol and 5 g of activated carbon were added, heated to reflux for 30 min, filtered, the filtrate was cooled and crystallized, filtered and dried to obtain 41.2 g of compound (II) 3-isobutylglutarimide with a yield of 91.2%. The NMR spectrum of the product is the same as in FIG. 1.

Step 2): Preparation of (R)-3-(carbamoylmethyl)-5-methylhexanoic acid: 40 g of compound (II) 3-isobutylglutarimide prepared in step 1) was added into a reaction flask, then 288 g of isopropanol, 72 g of purified water and 5 g of ethyl chrysanthemate esterase (provided by Institute of Bioengineering, Huadong Medicine Co., Ltd., purity 98%) were also added, heated to 35° C., the temperature was kept and stirred for 20 h. After the reaction, the ethyl chrysanthemate esterase was removed by filtration, the reaction solution was distilled under reduced pressure, concentrated until about ⅙ of the volume was left, cooled to 0-5° C., stirred and crystallized for 1 h, filtered and dried to obtain 41.9 g of target product compound (III) (R)-3-(carbamoylmethyl)-5-methylhexanoic acid with a yield of 94.7%. The product enantiomeric excess value, i.e., the ee value was 99.94%. The NMR spectrum of the product is the same as in FIG. 2.

EXAMPLE 5

Step 1): Preparation of 3-isobutylglutarimide: 50 g of compound (I) 3-isobutylglutaric acid (producer: Dayang Chem (Hangzhou) Co., Ltd., purity 98%), 100 mL of toluene, 100 mL of xylene and 25 g of urea were added into a reaction flask, stirred and heated to 120° C., the temperature was kept, refluxed and stirred for 3 h, cooled to 0-15° C., stirred and crystallized for 1 h, filtered and dried to obtain 41.9 g of compound (II) 3-isobutylglutarimide with a yield of 92.7%. The NMR spectrum of the product is the same as in FIG. 1.

Step 2): Preparation of (R)-3-(carbamoylmethyl)-5-methylhexanoic acid: 40 g of compound (II) 3-isobutylglutarimide prepared in step 1) was added into a reaction flask, then 500 g of cyclohexanone, 100 g of purified water and 5 g of esterase EST12-7 from the deep sea of South China Sea (provided by South China Sea Institute of Oceanology, Chinese Academy of Sciences, purity 98%) were also added, heated to 40° C., the temperature was kept and stirred for 10 h. After the reaction, the esterase EST12-7 from the deep sea of South China Sea was removed by filtration, the reaction solution was distilled under reduced pressure, concentrated until about ⅒ of the volume was left, cooled to 0-10° C., stirred and crystallized for 1 h, filtered and dried to obtain 40.9 g of target product compound (III) (R)-3-(carbamoylmethyl)-5-methylhexanoic acid with a yield of 92.4%, product enantiomeric excess value ee.=99.90%. The NMR spectrum of the product is the same as in FIG. 2.

The invention claimed is:
1. A method for preparing (R)-3-(carbamoylmethyl)-5-methylhexanoic acid, the method comprising:
    reacting 3-isobutylglutaric acid with a nitrogen-containing reagent to produce 3-isobutylglutarimide;
    reacting the 3-isobutylglutarimide in a solvent with a biological enzyme to perform stereoselective ring-opening to produce (R)-3-(carbamoylmethyl)-5-methylhexanoic acid;
    wherein:
    the biological enzyme is lipase from *Carica papaya*, lipase from *Pseudomonas cepacia*, lipase from *Candida rugosa*, ethyl chrysanthemate esterase, or esterase EST12-7 from the deep sea of South China Sea; and
    the solvent is a miscible system of water and an organic solvent, and the organic solvent is ethanol, isopropanol, cyclohexanol, tetrahydrofuran, 1,4-dioxane, acetone, cyclohexanone, or a mixture of any two or more thereof.

2. The method of claim 1, wherein the nitrogen-containing reagent is selected from the group consisting of ammonia water, urea, a basic ammonium salt, and thiourea.

3. The method of claim 1, wherein the biological enzyme is in the form of immobilized enzyme particles, enzyme powder, cells or organelles containing the biological enzyme, or crude enzymes obtained by culturing enzyme-producing microorganisms.

4. The method of claim 1, wherein the biological enzyme and the 3-isobutylglutarimide have a mass ratio of 1:1-1:20.

5. The method of claim 4, wherein the biological enzyme and the 3-isobutylglutarimide have a mass ratio of 1:5-1:10.

6. The method of claim 1, wherein the water and the organic solvent have a mass ratio of 1:1-1:5.

7. The method of claim 1, wherein the 3-isobutylglutarimide and the solvent have a mass ratio of 1:5-1:50.

8. The method of claim 7, wherein the 3-isobutylglutarimide and the solvent have a mass ratio of 1:5-1:10.

9. The method of claim 1, wherein the reacting the 3-isobutylglutarimide is at a temperature range from 25° C. to 55° C.

10. The method of claim 9, wherein the reacting the 3-isobutylglutarimide is at a temperature range from 30° C. to 45° C.

11. The method of claim 1, wherein the reacting the 3-isobutylglutarimide is for a time from 8 h to 20 h.

12. The method of claim 11, wherein the reacting the 3-isobutylglutarimide is for a time from 10 h to 15 h.

13. The method of claim 1 further comprising reacting the (R)-3-(carbamoylmethyl)-5-methylhexanoic acid with bromine under basic conditions to produce pregabalin.

* * * * *